United States Patent [19]

Umemura et al.

[11] 4,364,844

[45] Dec. 21, 1982

[54] CATALYST FOR PRODUCTION OF UNSATURATED CARBOXYLIC ACID, PREPARATION THEREOF AND PRODUCTION OF UNSATURATED CARBOXYLIC ACID

[75] Inventors: Sumio Umemura; Kyoji Ohdan; Fumihiko Sakai; Kenichi Suzuki; Yasuo Bando; Toshihiko Hogami; Masataka Fuginaga, all of Ube, Japan

[73] Assignee: Ube Industries, Ltd., Yamaguchi, Japan

[21] Appl. No.: 184,178

[22] Filed: Sep. 4, 1980

[30] Foreign Application Priority Data

Sep. 4, 1979 [JP] Japan ................... 54-112421

[51] Int. Cl.$^3$ .................. B01J 27/18; B01J 21/00
[52] U.S. Cl. .................... 252/435; 252/437; 252/443; 252/455 R; 252/464; 562/535
[58] Field of Search ............. 252/435, 437, 456, 464; 562/535

[56] References Cited

U.S. PATENT DOCUMENTS

| | | | |
|---|---|---|---|
| 4,075,244 | 2/1978 | Akiyama et al. | 562/535 |
| 4,092,271 | 11/1978 | Sze | 252/464 X |
| 4,113,745 | 9/1978 | Strojny et al. | 252/464 X |
| 4,146,733 | 3/1979 | White et al. | 252/437 X |
| 4,174,459 | 11/1979 | Sakamoto et al. | 252/437 X |
| 4,225,466 | 9/1980 | Wada et al. | 252/435 |
| 4,238,359 | 12/1980 | Akiyama et al. | 252/437 |

*Primary Examiner*—Carl F. Dees
*Attorney, Agent, or Firm*—Burgess, Ryan and Wayne

[57] ABSTRACT

An improved catalyst suitable for use in the production of an unsaturated carboxylic acid by the catalytic vapor phase oxidation of an unsaturated aldehyde is provided. In this catalyst, a heat-resistant inorganic substance, such as alumina, silica-alumina and silicon carbide, having a particle diameter of 3 through 10 mm, an apparent porosity of 35 through 60%, a water absorption of 20 through 50%, an average pore diameter of not less than 40 microns, a specific surface area of not more than 2 m$^2$/g and a bulk specific gravity of 1.5 through 2.0 is used for supporting a composition containing molybdenum, phosphorus, vanadium and the alkali metals. The use of the above-mentioned carrier results in the advantages that the unsaturated carboxylic acid, such as methacrylic acid, can be selectively produced from the unsaturated aldehyde at a high yield and that the mechanical strength of the catalyst is remarkably improved.

14 Claims, No Drawings

CATALYST FOR PRODUCTION OF UNSATURATED CARBOXYLIC ACID, PREPARATION THEREOF AND PRODUCTION OF UNSATURATED CARBOXYLIC ACID

The present invention relates to an improved catalyst suitable for use in the production of unsaturated carboxylic acids, such as acrylic acid and methacrylic acid by the catalytic vapor phase oxidation of unsaturated aldehydes, such as acrolein and methacrolein. The present invention also relates to a method for preparing the above-mentioned catalyst and a process for producing unsaturated carboxylic acids from the catalytic vapor phase oxidation of unsaturated aldehydes by using the above-mentioned catalyst.

More specifically, the present invention relates to an improved catalyst for producing unsaturated carboxylic acids by the catalytic vapor phase oxidation of unsaturated aldehydes, which catalyst contains at least four constituent elements of molybdenum, phosphorus, vanadium and the alkali metals supported on a carrier.

Heretofore, various catalysts containing, as catalyst constituent elements, molybdenum, phosphorus vanadium, the alkali metals and oxygen, which are suitable for use in the production of unsaturated carboxylic acid, as well as various methods for preparing such catalysts by supporting the above-mentioned catalyst constituent elements on a carrier have been proposed in various publications. Typical examples of such publications are Japanese Patent Laid-Open Application No. 50-82013/1975 (Mo-P-V-K,Cs,Rb,Tl), ibid 51-113818/1976 (Mo-P-Cs-V,Nb,Ta), ibid 51113818/1976 (Mo-P-K-Cs-V), ibid 51-115413/1976 (P-Mo-X-Y; X=K,Rb,Cs,Tl; Y=V,Fe,Mn,Ni,Ta,W,Sb, Co,Nb,Zn,Cd,U,Bi,Sn), ibid 50-96522/1975 (Na,K,Rb,Cs-P-Mo-V), Japanese Patent Publication No. 54-13876/1979 (P-Mo-Tl,K,Rb, Cs,Sr,Ba,Zn,Cd; and, as additional elements, Si,Cr,Al,Ge,Ti, V,W,Bi,Nb,B,Ga,Pb,Sn, Co,Pd) and the like. These known catalysts containing molybdenum, phosphorus, vanadium, and the alkali metals are generally prepared by first mixing compounds containing the constituent elements of the catalyst, such as molybdenum compounds, phosphorus compounds, vanadium compounds, alkali metal compounds and the like, with each other in an aqueous medium; concentrating or drying the resultant composition to form a clay-like solid or powders; molding the clay-like solid or powders, and; then, calcining the molded or shaped composition.

However, these catalysts have disadvantages in that, since the above-mentioned concentrated or dried compositions in the form of a clay-like solid or powders are non-sticky, the moldability of the compositions is poor, and also, in that the catalysts prepared by calcining the molded or shaped compositions have poor mechanical strengths, including crushing strength and attrition resistance.

On the other hand, catalysts containing, as catalyst constituent elements, molybdenum, phosphorus, vanadium and the alkali metals can be prepared by mixing the above-mentioned catalyst compositions and appropriate carriers, whereby the catalyst compositions are supported on the carriers, and by calcining the resultant carriers. However, in the case where these catalysts are used in the vapor phase oxidation of the unsaturated aldehydes, the yield of the desired unsaturated carboxylic acid remarkably decreases, compared to the above-mentioned catalysts prepared without using carriers. Furthermore, the attrition resistance of the above-mentioned supported catalysts is not sufficient to allow the use of these catalysts in commercial production plants. For instance, in the case where these catalysts are filled in reactors or where these catalysts are transported, there are disadvantages in that the catalyst constituent components are stripped from the carriers and the catalyst constituent components are powdered.

In addition, various means have been proposed to improve the moldability of the catalyst compositions in the preparation of the catalysts. For example, the addition of certain organic substances, such as polyvinyl alcohol, polyethylene glycol, cellulose, gelatin, stearic acid and the like, to the above-mentioned catalyst compositions before the calcination thereof or the mixture of the catalyst compositions and the carriers, or the addition of metal sulfates to the catalyst compositions have been proposed. However, these proposals are not effective for improving the attrition resistance of the above-mentioned catalysts.

Heretofore, the production of acrylic acid by the catalytic vapor phase oxidation of acrolein is commercially carried out. However, methacrylic acid has not been commercially produced from methacrolein by catalytic vapor phase oxidation. Catalysts which have high mechanical strength and which selectively catalyze the oxidation of the aldehyde group of methacrolein to produce methacrylic acid in a high yield without oxidizing the methyl group of methacrolein have not been developed.

Although the above-mentioned catalysts containing, as catalytic components, molybdenum, phosphorus, vanadium and the alkali metals result in a relatively high yield in the production of methacrylic acid by the catalytic vapor phase oxidation of methacrolein, the mechanical strength, especially the attrition resistance, of the catalysts are not sufficient to allow the use of the catalysts as a commercial catalyst and further improvement of the yield of the methacrylic acid is desired from a commercial point of view.

Accordingly, an object of the present invention is to obviate the aforementioned disadvantages of the prior art and to provide a catalyst containing molybdenum, phosphorus, vanadium and the alkali metals, which is suitable for use in the production of an unsaturated carboxylic acid, such as acrylic acid and methacrylic acid, by the vapor phase oxidation of an unsaturated aldehyde, such as acrolein and methacrolein, and which has excellent mechanical strength, including crushing strength, attrition resistance and the like.

Another object of the present invention is to provide a method for preparing the above-mentioned catalyst. A further object of the present invention is to provide a process for producing an unsaturated carboxylic acid such as acrylic acid and methacrylic acid, especially methacrylic acid, by the vapor phase oxidation of an unsaturated aldehyde, such as acrolein and methacrolein, especially methacrolein, at a high yield without causing undesirable side reactions.

Other objects and advantages of the present invention will be apparent from the following description.

In accordance with the present invention, there is provided a catalyst containing molybdenum, phosphorus, vanadium and the alkali metals supported on a carrier which is used for the production of an unsaturated carboxylic acid by the catalytic vapor phase oxidation of an unsaturated aldehyde and which is prepared by mixing a composition containing the constituent elements of the catalyst with the carrier, whereby the composition is supported on pores of the carrier, followed by calcination. The present inventors have found that, where a heat-resistant inorganic substance having pores with special physical properties is used as a carrier, a catalyst composition at least containing molybdenum, phosphorus, vanadium and the alkali metals can be supported on the carrier only by admixing the catalyst composition with the carrier, followed by a calcination, without molding or shaping the catalyst composition by a molding machine. A substantial amount of the catalyst composition is deposited on the walls of the pore portions of the carrier and, after the calcination, the catalyst having a content of the catalytic components of about 30 through about 60% by weight, based on the total weight of the catalyst, and having excellent mechanical strength and a high activity is obtained. Therefore, according to the present invention, at least one heat-resistant inorganic substance having a particle diameter of 2 through 10 mm, preferably 3 through 10 mm, an apparent porosity of 35 through 60%, a water absorption of 20 through 50%, an average pore diameter of not less than 40 microns, a specific surface area of not more than 2 m²/g and a bulk specific gravity of 1.5 through 2.0 is used as a carrier.

In accordance with the present invention, there is also provided a method for preparing a catalyst containing molybdenum, phosphorus, vanadium and the alkali metals supported on a carrier which is used for the production of an unsaturated carboxylic acid by the catalytic vapor phase oxidation of an unsaturated aldehyde, comprising the steps of:

(a) admixing a composition containing the constituent elements of the catalyst with the above-mentioned carrier, whereby the composition is supported in pores of the carrier, and;

(b) calcining the composition supported on the carrier.

In accordance with the present invention, there is further provided a process for producing an unsaturated carboxylic acid from an unsaturated aldehyde comprising the step of reacting the unsaturated aldehyde with molecular oxygen, at an elevated temperature, in the vapor phase in the presence of the above-mentioned catalyst containing molybdenum, phosphorus, vanadium and the alkali metals supported on the above-specified carrier.

The average pore diameter used herein is measured according to the mercury pressure porosimeter method as follows: 0.5 g of a sample (carrier) is put into a dilatometer. After the dilatometer is evacuated to $2 \times 10^{-2}$ mmHg or less by a vacuum pump, mercury is introduced into the dilatometer and, then, the dilatometer is charged in an autoclave. The autoclave is gradually pressurized from an atmospheric pressure up to 1500 kg/cm² (gauge pressure) and the decrease in the level of the mercury is continuously monitored. From the correlation between the pressure change and the level change of the mercury (i.e. the decrease in the volume of the mercury), the pore distribution is measured and, thus, the average pore diameter is determined.

The specific surface area (m²/g) of the carrier used herein is determined according to the BET method based on nitrogen gas adsorption.

The apparent porosity (%), the water absorption (%) and the bulk specific gravity used herein are determined, according to the method of JIS (Japanese Industrial Standard) R-2205 (1974), by the following equations.

$$\text{Apparent Porosity (\%)} = \frac{W_3 - W_1}{W_3 - W_2} \times 100$$

$$\text{Water Absorption (\%)} = \frac{W_3 - W_1}{W_1} \times 100$$

$$\text{Bulk Specific Gravity} = \frac{W_1}{W_3 - W_2}$$

wherein $W_1$: Weight (g) of the sample (log of the carrier) in the dry state
$W_2$: Weight (g) of the sample in water
$W_3$: Weight (g) of the water-saturated sample The catalyst according to the present invention contains the supported catalyst components not in a state such that the catalytic components cover only the surface of the carrier, but in a state such that substantially all of the catalyst components enter into the inside of the pores of the catalyst and are deposited on the inner surface thereof. As a result, mechanical strength, including crushing strength, attrition resistance and the like, but especially the attrition resistance, of the catalyst are remarkably improved as compared with any conventional catalyst for the production of unsaturated carboxylic acids, and the stripping of the catalyst components from the catalyst and the powdering of the catalyst components are advantageously prevented. Especially, in the case where the present catalyst is used in the production of methacrylic acid, both the conversion of methacrolein and the selectivity to methacrylic acid become high and, therefore, methacrylic acid can be produced at a high yield.

Furthermore, according to the present invention, neither the catalyst composition nor the admixture of the catalyst composition and the carrier need to be molded or shaped by using a tableting machine, an extruder and the like in the preparation of the catalyst. Consequently, the decrease in the catalytic activity and the fluctuations of the mechanical strength of the catalyst due to the molding operation can be advantageously prevented and, also, the catalyst having constant mechanical strength and having excellent reproducibility can be readily obtained.

The heat-resistant inorganic substances used, as a carrier, in the present invention can be those which are conventionally employed, as a carrier, in the conventional oxidation cataysts. Preferable heat-resistant inorganic substances employed in the present invention are alumina, silica-alumina, silicon carbide and the like. Most preferable substance is alumina, especially alpha-alumina. The heat-resistant inorganic substances are preferably in the form of a sphere or shapes similar to a sphere. The inorganic substances preferably have a particle diameter which is suitable for use in a fixed bed reactor. The particle diameter of the inorganic substance is generally within the range of 2 to 10 mm, preferably 3 to 10 mm and, more preferably, 3 to 8 mm.

As mentioned hereinabove, the apparent porosity, the water absorption, the average pore diameter, the specific surface area and the bulk specific gravity of the carrier are essential factors for achieving the objects of the present invention, and these factors are closely related to each other and greatly affect the mechanical strength of the catalyst, the catalytic activity, the amount of catalyst components supported on the carrier, the supported conditions of the catalyst components and the like.

According to the present invention, the apparent porosity of the carrier should be within the range of 35 to 60%, preferably 40 to 60% and, the water absorption should be within the range of 20 to 50%, preferably 20 to 45%. Although these two factors are related to the other factors mentioned above, in a case where the carrier having an apparent porosity and a water absorption within the above-specified ranges is employed, a large amount of the catalyst components can be supported on the carrier and the mechanical strength of the catalyst thus obtained is excellent. For instance, in a case where a carrier having an apparent porosity of less than 35% and a water absorption of less than 20% is employed, the amount of the catalyst components supported on the pores of the carrier is less than 30% by weight and the catalytic activity is poor, so that the desired conversion of, for example, methacrolein, and the desired yield of, for example, methacrylic acid, cannot be obtained. Contrary to this, in a case where the apparent porosity and the water absorption of the carrier are higher than the upper limits of the above-mentioned ranges, a catalyst having sufficient mechanical strengths (including crushing strength and attrition resistance) to allow the use of the catalyst as a commercial catalyst cannot be obtained, although the amount of the catalyst components supported on the pores of the carrier is increased.

The average pore diameter of the carrier employed in the present invention should be 40 microns or more, preferably 50 through 150 microns and, the specific surface area should be 2 m$^2$/g or less, preferably 1 m$^2$/g or less. In a case where the average pore diameter is less than 40 microns, the amount of the catalyst components supported on the pores of the carrier becomes too small and a catalyst having poor catalytic activity is obtained. The average pore diameter is preferably as large as possible, although the average pore diameter is closely related to the other factors, such as the apparent porosity, the water absorption and the like. However, since the mechanical strength of the catalyst become poor when the average pore diameter is large, the above-specified range of the average pore diameter is preferable. In a case where the specific surface area of the carrier is more than 2 m$^2$/g, the chemical property of the carrier itself adversely affects the catalytic activity and, as a result, a catalyst, which provides excellent reaction results, is difficult to obtain.

Furthermore, the bulk specific gravity of the carrier employed in the present invention should be within the range of 1.5 to 2.0, preferably 1.6 to 2.0. The bulk specific gravity of the carrier mainly affects the mechanical strength of the carrier. However, in a case where the bulk specific density is not within the above-specified range, the mechanical strength of the prepared catalyst becomes too weak or too strong and, as a result, the catalyst is not suitable for use in the commercial production of unsaturated carboxylic acids by the vapor phase oxidation of unsaturated aldehydes.

Although the amount of the catalyst components supported on the carrier is not critically limited, the amount is generally within the range of 30 to 60% by weight, preferably 35 to 55% by weight, based on the total weight of the catalyst. It is preferable that a substantial amount of the catalyst components be supported on the pores of the carrier. In a case where the amount of the supported catalyst components is too small, the desired catalytic activity cannot be obtained. Contrary to this, in a case where the amount of the supported catalyst components is too large, the mechanical strength, especially the attrition resistance, of the catalyst become poor. Accordingly, the above-specified range of the amount of the supported catalyst components is preferable.

As mentioned hereinabove, the present catalyst suitable for use in the production of unsaturated carboxylic acid and containing, as essential constituent elements, molybdenum, phosphorus, vanadium and the alkali metals, supported on the above-mentioned catalyst, can be prepared by (a) admixing a composition at least containing the above-mentioned essential constituent elements with the carrier to support the composition on the carrier and (b) calcining the composition supported on the carrier. More specifically, compounds containing the above-mentioned catalyst constituent elements, that is, molybdenum compounds, phosphorus compounds, vanadium compounds, the alkali metal compounds and the like, are used as starting materials. These compounds are mixed with each other in an aqueous medium and the composition thus obtained is then admixed with the carrier. Thus, the composition is supported on the pore portions of the carrier. The supported carrier is then calcined. The composition obtained from the mixing of the compounds containing the above-mentioned catalyst constituent elements in an aqueous medium may be in the form of slurry, clayey solid, powders and the like. The carrier can be used in a dry state or in a wet state, which is obtained, for example, by the addition of a small amount of water.

The admixing of the composition containing the catalyst constituent elements with the carrier can be carried out in any conventional manner. For instance, the carrier in a dry or wet state may be added to and mixed with the composition in the form of slurry or vice versa. Especially when the composition in the form of a powder is added to and mixed with the carrier in a wet state, the supported condition of the catalyst constituent elements on the carrier becomes excellent and a catalyst having excellent catalytic activity and mechanical strengths can be preferably obtained.

The admixing ratio of the composition containing the catalyst constituent elements to the carrier is generally within the range of 40 to 150 parts by weight (dry basis), preferably 50 to 140 parts by weight (dry basis), based on 100 parts by weight (dry basis) of the carrier, although this ratio is somewhat changed, depending upon the kinds of the carrier and the properties of the composition. In a case where the amount of the composition to the carrier is too large, the entire surface of the carrier is liable to be covered with the composition and the composition cannot readily enter into the deep portions of the pores of the carrier. As a result, since a substantial amount of the catalyst composition cannot be supported on the inside of the pores of the carrier, stripping and powdering of the catalyst components can occur. Contrary to this, in a case where the amount of said composition is too small, the catalytic activity of the resultant catalyst decreases, due to the fact that the amount of the catalyst components supported on the carrier becomes small. For these reasons, the above-specified range of the admixing ratio is preferable.

The admixing of the composition containing the catalyst constituent elements with the carrier can be carried out by using any conventional mixing device, so long as the carrier is not crushed by the mixing operation. For instance, the carrier in a wet state can be advantageously admixed with the catalyst composition in the form of powder by means of a rotary granulator. The mixing time can be, for example, 20 minutes through 5 hours, preferably, 30 minutes through 2 hours. By the mixing operation, the composition containing the catalyst constituent elements is supported on the pores of the carrier in such a state that the composition deeply enters into the pores of the carrier.

After the composition containing the catalyst constituent elements is supported on the carrier and, optionally, is dried, the calcination is carried out. The calcination temperature is generally within the range of 350° to 450° C., preferably 380° to 420° C. If the calcination temperature is too high, the catalytic activity is liable to become low. Contrary to this, if the calcination temperature is too low, the desired catalytic activity also cannot be obtained. Therefore, the calcination is suitably carried out at a temperature within the above-specified range. The calcination time is generally within the range of 3 to 20 hours, preferably 5 to 10 hours. The calcination of the catalyst is generally carried out under an atmosphere of an oxygen containing gas (e.g. air) or a starting gas mixture for the production of the unsaturated carboxylic acids (e.g. a gas mixture of methacrolein, oxygen, steam and nitrogen).

Although the compositions of the catalyst components supported on the carrier are not critically limited, the compositions of the catalyst components containing molybdenum, phosphorus, vanadium and the alkali metals and having the following general formula are preferable in order to produce unsaturated carboxylic acids such as methacrylic acid at a high yield.

$$Mo_aP_bV_cA_dO_e$$

wherein Mo is molybdenum, P is phosphorous, V is vanadium, A is the alkali metals, preferably at least one metal selected from the group consisting of potassium, cesium and rubidium and O is oxygen; the subscripts a, b, c, d and e represent the number of atoms, and when a is 12; b=0.5 to 3, preferably 0.8 to 1.5; c=0.05 to 2, preferably 0.1 to 1.5; d=0.1 to 3 preferably 0.5 to 2.8, and e is the number which is required by the total valance of the other atoms. Although, in the above-mentioned general formula, 2 atoms or less, in total, of at least one element selected from Ag, Al, Ca, Cu, Ba, Mg, Mn, Pb, Sr and the like, based on 12 atoms of Mo, may be further present in the catalysts, the desired catalytic activity and the desired mechanical strength of the ctalyst is not adversely affected.

Compounds containing the constituent elements of the catalyst used, as starting materials, in the preparation of the catalyst, such as, for example, molybdenum compounds, phosphorus compounds, vanadium compounds and the alkali metal compounds, can be any compounds which are generally used for the preparation of the conventional oxidation catalyst. Examples of such compounds are molybdenum compounds, such as molybdenum trioxide, 12-molybdophosphoric acid, 18-molybdodiphosphoric acid, ammonium molybdate and the like; phosphorus compounds, such as the ammonium salts or orthophosphoric acid, metaphosphoric acid, phosphorous acid, phosphoric acid and the like; vanadium compounds, such as vanadium pentoxide, ammonium metavanadate, vanadyl sulfate, vanadium tetrachloride and the like, and; nitrates, sulfates, carbonates, chlorides, of the alkali metals, such as potassium, cesium and rubidium, and the like.

The catalyst according to the present invention is generally prepared in the following manner. The compounds containing the constituent elements of the catalyst, for example, molybdenum compounds, phosphorus compounds, vanadium compounds and alkali metal compounds, for example, 12-molybdophosphoric acid, potassium nitrate and ammonium metavanadate, are mixed with each other in an aqueous medium and the resultant mixture is then dried at a temperature of 100° through 250° C., preferably 120° through 220° C., for 5 through 20 hours, preferably 6 through 16 hours. Thus, the catalyst composition, in the form of a powder, containing molybdenum, phosphorus, vanadium and potassium is formed. Then, a given amount of the carrier, which is wetted with a small amount of water, and the above-mentioned catalyst composition are admised with each other in a mixing device. Thus, the catalyst composition is supported on the pores of the carrier in such an amount that the amount of the catalyst composition supported on the carrier is within the range of 30 to 60% by weight, preferably 35 to 55% by weight, based on the total weight of the catalyst. The composition thus supported on the carrier is dried at a temperature of 100° through 130° C. and, then, calcined at a temperature of 350° through 450° C., preferably 380° through 420° C., under an atmosphere of air. Furthermore, when the catalyst composition is admixed with the carrier in the preparation of the catalyst, organic substances, such as polyvinyl alcohol, polyethylene glycol, gelatine, cellulose, stearic acid and the like, and sulfates, such as copper sulfate, aluminum sulfate, calcium sulfate and the like, can be added to the admixture.

According to the present invention, unsaturated aldehydes such as acrolein and methacrolein are reacted with molecular oxygen in a vapor phase, at an elevated reaction temperature, in the presence of the catalyst prepared as mentioned above, whereby unsaturated carboxylic acids such as acrylic acid and methacrylic acid are produced in a high yield. As the molecular oxygen, pure oxygen gas can, of course, be employed. However, since a high purity of oxygen is not required in the present process, air is usually employed from an economical point of view.

It is not necessary to employ, as a starting material, unsaturated aldehydes such as acrolein and methacrolein having a high purity.

The catalytic process according to the present invention may be carried out in the presence of a diluent which does not adversely affect the present reaction. Examples of such diluents are nitrogen, carbon dioxide, steam or the like. Of these diluents, steam not only improves the selectivity to the unsaturated carboxylic acid such as acrylic acid and methacrylic acid, but also, prolongs the life of the catalytic activity. Therefore, the catalytic vapor phase oxidation reaction of the present invention can be advantageously carried out by the addition of steam to the reaction system.

The process of the present invention can be carried out under normal pressure, elevated pressure or reduced pressure, but, in general, normal pressure can be conveniently used. The reaction temperature is preferably within the range of 250° to 400° C. and, more preferably, 280° to 360° C. The contact time in a reactor is preferably within the range of 0.1 to 15 seconds and, more preferably, 0.5 to 10 seconds. The process according to the present invention is generally carried out by using a mixed gas containing unsaturated aldehyde such as acrolein or methacrolein, molecular oxygen (e.g. air) and steam. Although the composition of the mixed gas may be varied over a wide range, typical examples of the composition of the mixed gas are 0.5 to 7 moles and, more preferably, 1 to 5 moles, of moleculr oxygen, and 1 to 30 moles and, more preferably, 2 to 10 moles, of steam, based on 1 mol of the unsaturated aldehydes such as acrolein and methacrolein. The unsaturated carboxylic acids such as acrylic acid and methacrylic acid thus produced can be recovered according to any of the conventional techniques, such as condensation, solvent extraction and the like.

The catalyst according to the present invention can be effectively used, especially in a fixed reactor.

The present invention now will be further illustrated by, but is by no means limited to, the following Examples together with Comparative Examples.

In the Examples and the Comparative Examples, the conversion (%), the selectivity (%) and the yield (%) were determined based on the data obtained after 2 hours of operation by the following equations.

$$\text{Conversion (\%)} = \frac{\text{Moles of acrolein or methacrolein reacted}}{\text{Moles of acrolein or methacrolein fed}} \times 100$$

$$\text{Selectivity (\%)} = \frac{\text{Moles of acrylic acid or methacrylic acid produced}}{\text{Moles of acrolein or methacrolein reacted}} \times 100$$

$$\text{Yield (\%)} = \frac{\text{Moles of acrylic acid or methacrylic acid produced}}{\text{Moles of acrolein or methacrolein fed}} \times 100$$

The supported amount of the catalyst compoents on the carrier was determined according to the following equation.

$$\text{Supported Amount (\%)} = \frac{\text{Total Weight (g) of Catalyst} - \text{Weight (g) of Carrier}}{\text{Total Weight (g) of Catalyst}} \times 100$$

The mechanical strengths of the catalyst were determined as follows.

(1) Crushing Strength (kg)

The crushing strength of the catalyst was measured by using a Kiya-type hardness meter. In this test method, a sample was first place on a sample table and a load was then added onto the sample. Thus, the crushing strength was represented by the load (kg) when the sample was crushed. Each result shown in the Tables below is an average of the results obtained from 30 test samples.

(2) Drop Attrition Rate (%)

20 g of catalyst particles (sample) were dropped from the top of a glass cylinder tube having a diameter of 1 inch and a height of 3000 mm. The glass cylinder was vertically installed and the bottom of the tube was covered with a screen having an opening size of 8 mesh. The powders which passed through the 8 mesh screen were weighed and the drop attrition rate (%) was determined by the following equation.

$$\text{Drop Attrition Rate (\%)} = \frac{\text{Powder Weight (g)}}{\text{Sample Catalyst Weight (20g)}} \times 100$$

(3) Shaking Attrition Rate (%)

20 g of catalyst particles (sample) were placed in a 100 ml glass conical flask and shaken up and down for 30 minutes on a shaker. Thereafter, the catalyst particles were taken out and weighed. The shaking attrition rate (%) was determined by the following equation.

$$\text{Shaking Attrition Rate (\%)} = \frac{\text{Sample Catalyst Weight (20g)} - \text{Catalyst Weight (g) after Shaking}}{\text{Sample Catalyst Weight (20g)}} \times 100$$

EXAMPLE 1

100 ml of water was added to 791.1 g of a 50% by weight aqueous 12-molybdophosphoric acid ($H_3PMo_{12}O_{40}.30H_2O$) solution and heated to a temperature of about 40° C., while stirring. To this solution, an aqueous solution, which was obtained by dissolving 38.8 g of potassium nitrate into 75 ml of water, was added and, after stirring, 7.9 g of ammonium metavanadate ($NH_4VO_3$) in the form of a powder was added to the mixture with stirring, while warming. Thus, a slurry was obtained. After the slurry was concentrated and evaporated, the residue was further dried at a temperature of 130° C. for 10 hours and, then, ground to form a catalyst composition, in the form of powder, containing molybdenum, phosphorus, vanadium and potassium.

Spherical alpha-alumina having a particle diameter of 5 mm and having an apparent porosity of 48%, a water absorption of 27%, an average pore diameter of 90 microns, a bulk specific gravity of 1.75 and a specific surface area of less than 1 m²/g was used as a carrier. The carrier was wetted by the addition of a small amount of water.

60 g (dry basis) of the wet carrier was placed in a rotating dish of a rotary granulator. While the rotating dish was rotated at a speed of 25 rpm with a dish inclination angle of 40°, 40 g of the powdered catalyst composition obtained as mentioned above was spread over the carrier and mixed therewith for one hour. By the mixing in the rotary granulator, the powdered catalyst composition was supported on the carrier in a state such that the powdered catalyst composition entered deep into the pore portions of the carrier.

The carrier having the catalyst composition supported thereon was calcined at a temperature of 400° C., for 5 hours, in an air atmosphere. Thus, the desired catalyst was obtained.

The amount of the catalyst components supported on the carrier was 39% by weight and the composition of the catalyst components (atomic ratio) was as follows.

$Mo_{12}P_1V_{0.4}K_{2.20}$ wherein oxygen was omitted.

25 ml of the spherical catalyst thus obtained and having a diameter of 5 mm was packed into a glass reaction tube having an inner diameter of 14 mm and a length of 300 ml. A gas mixture containing methacrolein, oxygen, steam and nitrogen at a mol ratio of 1:2:5:17 was fed through the reactor at a flow rate of 200 ml/min and was catalytically reacted under the conditions of a temperature of 350° C. and a contact time of 7.5 sec.

The mechanical strength of the catalyst and the results of the catalytic reaction are shown in Table 2 below.

EXAMPLE 2 TO 8

Various catalysts having the compositions shown in Table 1 below were prepared in a manner as described in Example 1, except that the amonts of the starting materials were changed so as to obtain the catalysts having the compositions shown in Table 1. The amounts of the catalyst components on the carrier are shown in Table 1 below.

The catalytic vapor phase oxidation reactions of methacrolein were carried out in a manner as described in Example 1, except that the catalysts obtained as mentioned above were used.

The mechanical strength of the catalysts and the results of the catalytic reactions are shown in Table 2 below.

EXAMPLES 9 to 12

Various catalysts having the compositions shown in Table 1 below were prepared in a manner as described in Example 1, except that 4.04 g of cupric nitrate [Cu(NO$_3$)$_2$.3H$_2$O], 2.84 g of silver nitrate (AgNO$_3$), 3.95 of calcium nitrate [Ca(NO$_3$)$_2$.4H$_2$O] or 6.27 g of aluminum nitrate [Al(NO$_3$)$_3$.9H$_2$O] was added to the aqueous solution of 12-molybdophosphoric acid of Example 1. Thus, the catalysts having the amount of the catalyst components on the carrier listed in Table 1 below were obtained.

The catalytic vapor phase oxidation reactions of methacrolein were carried out in a manner as described in Example 1, except that the catalysts obtained as mentioned above were used.

The mechanical strength of the catalysts and the results of the catalytic reactions are shown in Table 2 below.

EXAMPLES 13 TO 17

Various catalysts having the composition shown in Table 1 below were prepared in a manner as described in Example 1, except that spherical carriers listed in Table 1 below were used in lieu of the alpha-alumina used in Example 1. The amounts of the catalyst compositions on the carriers, of the catalysts thus obtained are shown in Table 1 below.

By using the catalyst obtained in Example 13, the catalytic vapor phase oxidation reaction of methacrolein in Example 1 was repeated. The results are shown in Table 2 below.

With respect to the catalysts obtained in Examples 14 to 17, the catalytic vapor phase oxidation reactions of methacrolein were carried out in a manner as described in Example 1, except that the following reaction conditions were used.

| | |
|---|---|
| Catalyst Amount: | 20 ml |
| Reaction Tube: | Stainless steel, 16mm$^{100}$ × 400mm$^L$ |
| Gas Mixture: | Methacrolein:O$_2$:Steam:N$_2$ = 1:2.5:5:16.5 (mol ratio) |
| Feed Rate: | 200 ml/min |
| Reaction Temperature: | 350° C. |
| Contact Time: | 6 sec. |

The mechanical strength of the catalysts and the results of the catalytic reactions are shown in Table 2 below.

EXAMPLE 18

A catalyst having a composition shown in Table 1 below was prepared in a manner as described in Example 1, except that the cylindrical carrier listed in Table 1 was used in lieu of the alpha-alumina used in Example 1. The amount of the catalyst components on the carrier is shown in Table 1 below.

The catalytic vapor phase oxidation reaction of methacrolein was carried out in a manner as described in Example 1, except that the catalyst obtained as mentioned above was used.

The mechanical strength of the catalyst and the results of the catalytic reactions are shown in Table 2 below.

EXAMPLE 19

A catalyst having a composition shown in Table 1 below was prepared in a manner as described in Example 1, except that the amounts of the starting materials were changed so as to obtain the catalyst having the composition shown in Table 1 and the spherical carrier shown in Table 1 was used. The amount of the catalyst components on the carrier is shown in Table 1 below.

The catalytic vapor phase oxidation reaction of methacrolein was carried out in a manner as described in Example 1, except that the catalyst obtained as mentioned above was used.

The mechanical strength of the catalyst and the results of the catalytic reactions are shown in Table 2 below.

TABLE 1

| | Catalyst Component (Oxygen is omitted: Atomic Ratio) | | | | | Supported Amount (wt %) | Carrier (Examples 1–12 and 14–19: Alumina Example 13: Silicon Carbide) | | | | | | |
|---|---|---|---|---|---|---|---|---|---|---|---|---|---|
| Example No. | Mo | P | V | Alkali Metal | Additional Element | | Size | Shape | Apparent Porosity (%) | Water Absorption (%) | Average Pore Diameter (μ) | Specific Surface Area (m$^2$g) | Bulk Specific Gravity |
| 1 | 12 | 1 | 0.4 | K = 2.26 | 0 | 39 | 5mm φ | Sphere | 48 | 27 | 90 | 1 | 1.75 |
| 2 | 12 | 1 | 0.4 | K = 2.0; Cs = 0.3 | 0 | 40 | " | " | " | " | " | " | " |
| 3 | 12 | 1 | 0.4 | Cs = 2.3 | 0 | 39 | " | " | " | " | " | " | " |
| 4 | 12 | 1 | 0.4 | K = 1.5; Rb = 1.0 | 0 | 41 | " | " | " | " | " | " | " |
| 5 | 12 | 1 | 0.4 | Rb = 2.5 | 0 | 40 | " | " | " | " | " | " | " |
| 6 | 12 | 1.4 | 1 | K = 2.3 | 0 | 42 | " | " | " | " | " | " | " |
| 7 | 12 | 1.1 | 0.6 | K = 2.3 | 0 | 40 | " | " | " | " | " | " | " |
| 8 | 12 | 0.9 | 0.1 | K = 2.0; Cs = 0.3 | 0 | 41 | " | " | " | " | " | " | " |

TABLE 1-continued

| | Catalyst Component (Oxygen is omitted: Atomic Ratio) | | | | | | Carrier (Examples 1-12 and 14-19: Alumina Example 13: Silicon Carbide) | | | | | | |
|---|---|---|---|---|---|---|---|---|---|---|---|---|---|
| Example No. | Mo | P | V | Alkali Metal | Additional Element | Supported Amount (wt %) | Size | Shape | Apparent Porosity (%) | Water Absorption (%) | Average Pore Diameter ($\mu$) | Specific Surface Area ($m^2g$) | Bulk Specific Gravity |
| 9 | 12 | 1 | 0.4 | K = 2.26 | Cu = 0.1 | 40 | " | " | " | " | " | " | " |
| 10 | 12 | 1 | 0.4 | K = 2.26 | Ag = 0.1 | 40 | " | " | " | " | " | " | " |
| 11 | 12 | 1 | 0.4 | K = 2.26 | Ca = 0.1 | 41 | " | " | " | " | " | " | " |
| 12 | 12 | 1 | 0.4 | K = 2.26 | Al = 0.1 | 41 | " | " | " | " | " | " | " |
| 13 | 12 | 1 | 0.4 | K = 2.26 | 0 | 35 | 4mm φ | Sphere | 40 | 21 | 60 | 1 | 1.95 |
| 14 | 12 | 1 | 0.4 | K = 2.26 | 0 | 49 | 5mm φ | " | 52 | 30 | 100 | " | 1.70 |
| 15 | 12 | 1 | 0.4 | K = 2.26 | 0 | 47 | 4mm φ | " | 50 | 28 | 95 | " | 1.73 |
| 16 | 12 | 1 | 0.4 | K = 2.26 | 0 | 54 | 5mm φ | " | 56 | 36 | 110 | " | 1.65 |
| 17 | 12 | 1 | 0.4 | K = 2.26 | 0 | 53 | 8mm φ | " | 55 | 36 | 110 | " | 1.66 |
| 18 | 12 | 1 | 0.4 | K = 2.26 | 0 | 48 | 5mm φ × 5mm | Cylinder | 52 | 30 | 100 | " | 1.70 |
| 19 | 12 | 1 | 0.4 | K = 1.9 Cs = 0.4 | 0 | 54 | 5mm φ | Sphere | 56 | 36 | 110 | " | 1.65 |

TABLE 2

| | Result of Catalytic Reaction | | | Mechanical Strength of Catalyst | | |
|---|---|---|---|---|---|---|
| Example No. | Conversion of Methacrolein (%) | Selectivity to Methacrylic Acid (%) | Yield of Methacrylic Acid (%) | Crushing Strength (kg) | Drop Attrition Rate (%) | Shaking Attrition Rate (%) |
| 1 | 93.5 | 83.2 | 77.8 | 6.3 | 0.3 | 0.4 |
| 2 | 94.5 | 82.7 | 78.2 | 6.2 | 0.4 | 0.5 |
| 3 | 95.5 | 80.3 | 76.7 | 6.3 | 0.3 | 0.4 |
| 4 | 92.6 | 83.3 | 77.1 | 6.1 | 0.4 | 0.8 |
| 5 | 90.5 | 84.2 | 76.2 | 6.4 | 0.5 | 0.9 |
| 6 | 94.5 | 82.1 | 77.6 | 6.4 | 0.3 | 0.5 |
| 7 | 95.7 | 80.1 | 76.6 | 6.3 | 0.4 | 0.6 |
| 8 | 92.8 | 83.5 | 77.5 | 6.2 | 0.5 | 0.6 |
| 9 | 96.3 | 80.4 | 77.4 | 6.1 | 0.3 | 0.4 |
| 10 | 90.2 | 84.2 | 75.9 | 6.0 | 0.4 | 0.5 |
| 11 | 92.3 | 83.8 | 77.3 | 6.1 | 0.3 | 0.4 |
| 12 | 94.2 | 83.0 | 78.1 | 6.0 | 0.4 | 0.5 |
| 13 | 90.7 | 85.6 | 77.6 | 7.5 | 0.3 | 0.4 |
| 14 | 94.3 | 82.1 | 77.4 | 5.3 | 0.8 | 1.1 |
| 15 | 93.8 | 83.2 | 77.5 | 5.6 | 0.7 | 1.2 |
| 16 | 96.5 | 80.6 | 77.7 | 5.1 | 0.9 | 1.5 |
| 17 | 96.2 | 80.8 | 77.7 | 5.3 | 0.9 | 0.9 |
| 18 | 94.7 | 82.1 | 77.7 | 5.4 | 0.9 | 1.0 |
| 19 | 96.8 | 80.5 | 77.9 | 5.2 | 0.8 | 0.9 |

EXAMPLE 20

25 ml of the catalyst prepared in Example 1 was packed into a glass reaction tube having an inner diameter of 14 mm and a length of 300 mm. Thereafter, a gas mixture of acrolein, oxygen, steam and nitrogen at a mol ratio of 1:2:5:7 was fed through the reaction tube at a flow rate of 300 ml/min, and was catalytically reacted under the conditions of a reaction temperature of 350° C. and a contact time of 5.0 sec.

The conversion of acrolein was 94.5%, the selectivity to acrylic acid was 85.0% and the yield of acrylic acid was 80.3%.

COMPARATIVE EXAMPLE 1

A catalyst composition, in the form of a powder, prepared in a manner as described in Example 1 and containing molybdenum, phosphorous, vanadium and potassium was molded, by means of a tableting machine, to form a molded catalyst composition in the form of cylindrical tablets, each having a diameter of 5 mm and a height of 5 mm.

The molded catalyst composition was then calcined at a temperature of 400° C. for 5 hours in an air atmosphere. Thus, the catalyst (with no carrier) having the same composition of the catalyst components as that of Example 1 was obtained.

17 ml of the catalyst obtained above was packed into a glass reaction tube having a diameter of 14 mm and a length of 300 mm. A gas mixture of methacrolein, oxygen, steam and nitrogen at a mol ratio of 1:2:5:17 was fed through the reaction tube at a flow rate of 200 ml/min and was catalytically reacted under the conditions of a reaction temperature of 350° C. and a contact time of 5.1 sec.

The mechanical strengths of the catalyst and the results of the catalytic reaction are shown in Table 4 below.

Comparative Examples 2 to 5

Various catalysts were prepared in a manner as described in Example 1, except that spherical alpha-alumina particles each having a diameter of 5 mm shown in Table 3 below were used in lieu of the alpha-alumina particles of Example 1. The amounts of the catalyst components supported on the carrier were shown in Table 3 below.

The catalytic vapor phase oxidation reactions of methacrolein were carried out in a manner as described in Example 1, except that the catalysts obtained above were used.

The mechanical strength of the catalysts and the results of the catalytic reactions are shown in Table 4 below.

TABLE 3

| | Carrier | | | | | |
|---|---|---|---|---|---|---|
| Comparative Example | Apparent Porosity (%) | Water Absorption (%) | Average Pore Diameter ($\mu$) | Specific Surface Area ($m^2/g$) | Bulk Specific Gravity | Amount of Catalyst Component Supported on Carrier (wt %) |
| 2 | 38 | 17 | 10 | <1 | 2.10 | 25 |
| 3 | 55 | 32 | 0.1 | 6.6 | 1.60 | 21 |

TABLE 3-continued

| | Carrier | | | | | Amount of Catalyst Component Supported on Carrier (wt %) |
|---|---|---|---|---|---|---|
| Comparative Example | Apparent Porosity (%) | Water Absorption (%) | Average Pore Diameter (μ) | Specific Surface Area (m²/g) | Bulk Specific Gravity | |
| 4 | 23 | 8 | 25 | <1 | 2.50 | 18 |
| 5 | 65 | 55 | 0.01 | 220 | 1.10 | 10 |

Catalyst Component: $Mo_{12}P_1V_{0.4}K_{2.26}$ (Atomic Ratio)
($O_2$ is omitted.)

TABLE 4

| | Result of Catalytic Reaction | | | Mechanical Strength of Catalyst | | |
|---|---|---|---|---|---|---|
| Comparative Example | Conversion of Methacrolein (%) | Selectivity to Methacrylic Acid (%) | Yield of Methacrylic Acid (%) | Crushing Strength (kg) | Drop Attrition Rate (%) | Shaking Attrition Rate (%) |
| 1 | 97.0 | 75.0 | 72.3 | 1.0 | 13.5 | 15.6 |
| 2 | 60.8 | 83.6 | 50.8 | 12.6 | 15.3 | 16.8 |
| 3 | 53.0 | 58.6 | 30.7 | 8.5 | 18.6 | 19.2 |
| 4 | 45.6 | 83.2 | 37.9 | 15.0 | 8.6 | 10.8 |
| 5 | 42.1 | 45.2 | 18.9 | 5.5 | 8.5 | 9.6 |

We claim:

1. In a catalyst containing molybdenum, phosphorus, vanadium and the alkali metals supported on a carrier which is used for the production of an unsaturated carboxylic acid by the catalytic vapor phase oxidation of an unsaturated aldehyde, the catalyst being prepared by admixing a composition containing the constituent elements of the catalyst with the carrier, whereby the composition is supported on pores of the carrier, followed by calcination; the improvement wherein the catalyst is in the form of particulate particles and wherein the carrier is at least one heat-resistant inorganic substance having a particle diameter of 2 through 10 mm, an apparent porosity of 35 through 60%, a water absorption of 20 through 50%, an average pore diameter of not less than 40 microns, a specific surface area of not more than 2 m²/g and a bulk specific gravity of 1.5 through 2.0.

2. A catalyst as claimed in claim 1, wherein said heat-resistant inorganic substance has a particle diameter of 3 through 8 mm, an apparent porosity of 40 through 60%, a water absorption of 20 through 45%, an averge pore diameter of 50 through 150 microns, a specific surface area of not more than 1 m²/g and a bulk specific gravity of 1.6 through 2.0.

3. A catalyst as claimed in claim 1, wherein the admixing of the composition containing the constituent elements of the catalyst with the carrier is carried out by admixing the composition in the form of a powder with the carrier in a wet state.

4. A catalyst as claimed in claim 1, wherein said heat-resistant inorganic substance is at least one substance selected from the group consisting of alumina, silica-alumina and silicon carbide.

5. A catalyst as claimed in claim 4, wherein said alumina is alpha-alumina.

6. A catalyst as claimed in claim 1, wherein the amount of the catalyst components supported on the carrier is within the range of 30 to 60% by weight based on the total weight of the catalyst.

7. A catalyst as claimed in claim 1, wherein said catalyst has the general formula $$Mo_aP_bV_cA_dO_e$$

wherein Mo is molybdenum, P is phosphorus, V is vanadium, A is at least one alkali metal and O is oxygen; the subscripts a, b, c, d and e represent the number of atoms, and when a is 12, b=0.5 to 3, c=0.05 to 2, d=0.1 to 3 and e is the number which is required by the total valance of the other atoms.

8. A method for preparing a catalyst containing molybdenum, phosphorus, vanadium and alkali metal supported on a carrier which is used for the production of an unsaturated carboxylic acid by the catalytic vapor phase oxidation of an unsaturated aldehyde, comprising the steps of:
   (a) admixing a composition containing the constituent elements of the catalyst with the carrier, whereby the composition is supported on the walls of the pores of the carrier, said carrier being at least one heat-resistant inorganic substance having a particle diameter of 2 through 10 mm, an apparent porosity of 35 through 60%, a water absorption of 20 through 50%, an average pore diameter of not less than 40 microns, a specific surface area of not more than 2 m²/g and a bulk specific gravity of 1.5 through 2.0, and;
   (b) calcining the composition supported on the carrier.

9. A method as claimed in claim 8, wherein said heat-resistant inorganic substance has a particle diameter of 3 through 8 mm, an apparent porosity of 40 through 60%, a water absorption of 20 through 45%, an average pore diameter of 50 through 150 microns, a specific surface area of not more than 1 m²/g and a bulk specific gravity of 1.6 through 2.0.

10. A method as claimed in claim 8, wherein the admixing of the composition containing the constituent elements of the catalyst with the carrier is carried out by admixing the composition in the form of a powder with the carrier in a wet state.

11. A method as claimed in claim 8, wherein said heat-resistant inorganic substance is at least one substance selected from the group consisting of alumina, silica-alumina and silicon carbide.

12. A method as claimed in claim 11, wherein said alumina is alpha-alumina.

13. A method as claimed in claim 8, wherein the amount of the catalyst components supported on the carrier is within the range of 30 to 60% by weight based on the total weight of the catalyst.

14. A method as claimed in claim 8, wherein said catalyst has the general formula $$Mo_a P_b V_c A_d O_e$$

wherein Mo is molybdenum, P is phosphorous, V is vanadium, A is at least one alkali metal and O is oxygen; the subscripts a, b, c, d and e represent the number of atoms, and when a is 12, b=0.5 to 3, c=0.05 to 2, d=0.1 to 3 and e is the number which is required by the total valance of the other atoms.

* * * * *